(12) United States Patent
Sisken et al.

(10) Patent No.: US 10,328,213 B2
(45) Date of Patent: Jun. 25, 2019

(54) CELL INJECTION NEEDLE

(71) Applicant: Muffin Incorporated, West Lafayette, IN (US)

(72) Inventors: Richard B. Sisken, West Lafayette, IN (US); Ryan Pruchnic, Pittsburgh, PA (US); Frank J. Fischer, Jr., Bloomington, IN (US); Steven Charlebois, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 787 days.

(21) Appl. No.: 14/211,702

(22) Filed: Mar. 14, 2014

(65) Prior Publication Data

US 2014/0276368 A1    Sep. 18, 2014

Related U.S. Application Data

(60) Provisional application No. 61/789,518, filed on Mar. 15, 2013.

(51) Int. Cl.
| | |
|---|---|
| *A61M 5/34* | (2006.01) |
| *A61M 5/158* | (2006.01) |
| *A61M 25/00* | (2006.01) |
| *A61B 18/24* | (2006.01) |

(52) U.S. Cl.
CPC ............ *A61M 5/34* (2013.01); *A61M 5/1582* (2013.01); *A61B 18/24* (2013.01); *A61M 25/007* (2013.01); *A61M 25/0069* (2013.01)

(58) Field of Classification Search
CPC ...... A61M 5/34; A61M 5/158; A61M 5/1582; A61M 25/007; A61M 25/0069; A61M 5/1585; A61B 18/24

USPC .......................................... 604/22, 272, 506
See application file for complete search history.

(56) References Cited

U.S. PATENT DOCUMENTS

| | | | |
|---|---|---|---|
| 4,698,056 | A | 10/1987 | Ciannella |
| 6,120,520 | A | 9/2000 | Saadat et al. |
| 6,332,877 | B1 | 12/2001 | Michels |
| 6,344,027 | B1 | 2/2002 | Goll |
| 6,425,854 | B1 * | 7/2002 | Galt ................ A61B 17/00491 600/29 |
| 6,432,119 | B1 | 8/2002 | Saadat |
| 6,464,662 | B1 | 10/2002 | Raghavan et al. |
| 6,478,775 | B1 | 11/2002 | Galt et al. |
| 6,544,220 | B2 | 4/2003 | Shuman et al. |
| 6,549,803 | B1 | 4/2003 | Raghavan et al. |
| 6,572,579 | B1 | 6/2003 | Raghavan et al. |

(Continued)

OTHER PUBLICATIONS

International Search Report and Written Opinion issued in PCT/US2014/021699, dated May 7, 2014.

*Primary Examiner* — Imani N Hayman
*Assistant Examiner* — Tiffany Legette
(74) *Attorney, Agent, or Firm* — Woodard, Emhardt, Henry, Reeves & Wagner, LLP

(57) ABSTRACT

Methods and apparatus are provided for treating tissue with apparatus that includes an priming portion for initiating a healing response in the tissue to be treated, and which delivers a bioactive agent during or after preparing tissue adjacent the apparatus, as by generating or aiding a healing, regeneration or repair response in the tissue. The priming portion may comprise an abrasive surface, fluid ejection ports, and/or stimulation by electrical, thermal, or light energy.

15 Claims, 9 Drawing Sheets

(56) References Cited

U.S. PATENT DOCUMENTS

| | | |
|---|---|---|
| 6,749,833 B2 | 6/2004 | Raghavan et al. |
| 7,862,551 B2 | 1/2011 | Bates |
| 2004/0022864 A1 | 2/2004 | Freyman et al. |
| 2004/0158136 A1* | 8/2004 | Gough ............... A61B 5/14546 600/328 |
| 2006/0018941 A1 | 1/2006 | Matsuda et al. |
| 2008/0039776 A1 | 2/2008 | Ghabrial |
| 2008/0086111 A1 | 4/2008 | Cowan et al. |
| 2008/0125709 A1* | 5/2008 | Chang ................... A61M 29/00 604/96.01 |
| 2008/0294096 A1 | 11/2008 | Uber, III et al. |
| 2009/0131866 A1 | 5/2009 | Zhang et al. |
| 2010/0226903 A1 | 9/2010 | Morris et al. |
| 2010/0280493 A1 | 11/2010 | Nayak |
| 2010/0331814 A1 | 12/2010 | Bates |
| 2011/0014181 A1 | 1/2011 | Thornton |
| 2011/0040279 A1* | 2/2011 | Walsh ................. A61L 27/3834 604/506 |

* cited by examiner

CELL INJECTION NEEDLE

This application claims the benefit of U.S. Provisional Application Ser. No. 61/789,518, filed on Mar. 15, 2013, which is incorporated herein by reference in its entirety.

The present disclosure pertains generally to methods and apparatus for delivering cells into a body.

BACKGROUND

The failure of introduced cells to integrate into recipient tissue continues to be a problem. Oftentimes, the cells are delivered in tiny pockets or pools with many of the cells having no contact with surrounding tissue. Additionally, many of the cells that do contact the surrounding tissue are unable to find an acceptable location for integration. Therefore excess cells are typically injected, and the cells have substantial difficulty in providing their therapeutic function to the surrounding tissue. Thus, there is a need for improvement in this field.

SUMMARY

In certain aspects, the present disclosure provides cell delivery systems and methods that improve the integration of cells into a patient's tissue. In accordance with some forms of the disclosure, such systems and methods are configured to prime a particular tissue location (e.g. generate or help generate a healing, repair, regeneration or similar response) in a patient prior to that tissue location receiving a plurality of cells. Specifically, at least one embodiment of a method of delivering cells includes inserting a surgical needle with a needle shaft, a needle tip, and a priming portion adjacent to the needle tip and arranged to prime (e.g. contact or otherwise affect, to generate a response as noted above) adjacent tissue into the tissue of a human body; operating the priming portion to prepare adjacent tissue; and releasing a plurality of cells from the tip region of the needle so as to deliver cells toward the prepared tissue.

In certain embodiments, the cell delivery system has an elongated needle body having a longitudinal axis, a first portion, a second portion, and a tissue penetrating distal tip. The first portion and second portion are capable of transitioning from a first position for insertion into tissue into a second position for delivery of cells into the tissue, and the first and second portions define a first cavity capable of holding a plurality of cells when the needle body is in the first position. The first cavity may be in communication with tissue when the needle is in the second position.

Embodiments of a cell delivery system can include an elongated body having a priming portion, a cell-carrying portion, and a terminating or distal tissue-penetrating portion. The tissue-penetrating portion is arranged to penetrate tissue as the tissue-penetrating portion is forced into tissue. The priming portion is positioned adjacent to the tissue-penetrating portion and arranged to prepare tissue adjacent to the priming portion, e.g. to promote a regeneration or repair response in the prepared tissue. The cell-carrying portion is arranged to deliver a plurality of cells to tissue adjacent to the needle body.

Some embodiments of the cell delivery system comprise a syringe and a hollow needle. The syringe allows a user to easily load cells into the device and/or transport the cells from the syringe through the needle. The needle may have an elongated needle body and may be used to penetrate tissue, prime an internal tissue site during or after insertion of the needle, and/or deliver cells. It will be understood that "syringe" and "needle" are exemplary modes, and substitutes for these components or alternative structures may be used in specific embodiments. For example, devices such as pumps, power injectors, indeflators, compressible bladders, and the like may all be used as a substitute for a syringe. Furthermore, the term "needle" may include hypodermic needles, cannulas, microneedles, and nanoneedles.

Some embodiments of the cell delivery system include a syringe, a hollow needle, and cells to be delivered to injured tissue. Use of the term "cells" in this disclosure may include cells suspended in media or a carrier material such as a gel. It will be understood that use of the term "cells" in the disclosure may also include cells pre-attached to solid or semi-solid material piece(s). For example, the cells/cellular material may be an extracellular matrix (ECM) and/or a scaffold-like matrix. This matrix may have an all natural structure and/or composition. One example of such a matrix is porcine small intestinal submucosa (SIS).

The cells may be provided by a manufacturer preloaded in or on the device, or in a separate container or arrangement to be incorporated into or onto the delivery device prior to or during the cell delivery procedure. The cells (whether with or without a medium or carrier material) can be loaded into or onto a needle followed by flushing fluid (saline, media, etc.) to keep the cells near the tip. Alternatively, one may skip the loading step and instead directly flush the cells into position at the tip or at a location inside of tissue.

Several embodiments of the cell delivery system comprise a syringe and a hollow needle having a priming portion adjacent to the tissue-penetrating tip. In some embodiments, the syringe may be used to operate a priming portion of the needle. For example, the syringe may cause a physical movement of the priming portion. The priming portion may rotate, actuate, or otherwise move relative to the shaft portion of the needle or the tip portion of the needle. Alternatively, the syringe may cause the priming portion to move relative to the adjacent tissue.

The priming portion, in particular embodiments, contacts or otherwise affects adjacent tissue so as to increase the surface area of tissue receiving the delivered cells and/or trigger a regeneration, repair or healing response that is favorable to acceptance and utilization of the delivered cells. The syringe may power the priming portion or directly affect adjacent tissue by pressure or vacuum, such as by injecting saline in one or more pulses at high pressure toward or into the tissue of interest. These embodiments may also include cells to be delivered to primed tissue, such as from a preloaded portion of the device.

Some embodiments of the cell delivery system comprise a mechanical, electrical, thermal power source, or light source for or associated with the priming portion. For example, a motor or an actuator may be directly or indirectly connected to the priming portion of the needle so as to manipulate the priming portion to affect adjacent tissue. Additionally or alternatively, an electrical power source, thermal power source, and/or light source may be connected to the priming portion of the needle. These sources may either power the priming portion so as to prepare adjacent tissue or the energy from these sources may be transferred directly into the adjacent tissue. For example, electrical pulses from a pulse generator may be delivered to the priming portion so as to cause it to move and prepare the adjacent tissue. Alternatively, the electrical pulses may be applied to the surrounding tissue. A thermal power source may be connected to a priming portion to transfer heat to or from the priming portion and/or the tissue adjacent to the priming portion. Similarly, a light source such as a laser may be used to power the priming portion and/or directly affect to the adjacent tissue. Laser interstitial thermal therapy (LITT) and laser ablation are a few examples of using lasers to prime the tissue.

Some embodiments comprise a hollow needle capable of transitioning from a first position into a second position. The first position may be a needle configuration for insertion of the needle to the target tissue, and the second position may be a needle configuration for the priming and/or the delivery of the cells to the tissue. The cells may be delivered by flushing them through and/or from the needle, by passive Brownian motion, or by movement of the assembly or portions of the assembly.

Methods of delivering cells are disclosed with some methods including the steps of inserting a surgical needle with a needle shaft and a tip region into tissue of a human body; operating the surgical needle to prime tissue at the particular internal site following insertion of the needle; and releasing a plurality of cells from the tip region of the needle so as to deliver cells toward the primed tissue.

Further forms, objects, features, aspects, benefits, advantages, and embodiments of the present disclosure will become apparent from a detailed description and drawings provided herewith.

DESCRIPTION OF THE ILLUSTRATED EMBODIMENTS

Figure 1:
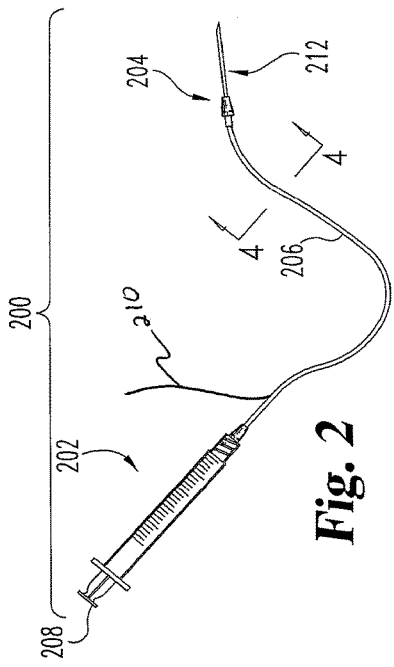
FIG. 1 is a side view of one embodiment of the cell delivery system.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. At least one embodiment is illustrated in detail, although it will be apparent to those skilled in the relevant art that some features that are not relevant to the present disclosure may not be illustrated for the sake of clarity.

FIG. 1 illustrates one embodiment of a cell delivery system 100. System 100 in that embodiment includes at least two components, a syringe 102 and an elongated, hollow needle 104. Syringe 102 includes a connecting portion 106 in this embodiment to connect syringe 102 to needle 104 and to at least a first operating member 108 (e.g. a plunger). Operating member 108 may be used to pressurize one or more chambers inside of the syringe, so as to force the contents of the syringe through the connecting portion 106 and through the needle 104. This embodiment of syringe 102 has a second operating member 110 that may be used to operate an priming portion 112 on needle 104. Operating member 110 may also be used to transition the needle from a first configuration or position into a second configuration or position. The first position is a needle configuration for insertion of needle 104 to the target tissue, and the second position is a needle configuration for engaging or otherwise affecting particular or selected tissue to prepare it (e.g. for accepting application(s) of cells), and/or for the delivery of the cells to the tissue.

In this particular embodiment, cells (not visible) are positioned inside syringe 102 and/or needle 104 prior to the delivery of the cells inside the tissue of a patient. The cells may be preloaded inside syringe 102 and/or needle 104 after manufacturing of system 100 (syringe 102 and needle 104 in parts or together) or they may be loaded immediately prior to the cell delivery procedure.

Figure 2:
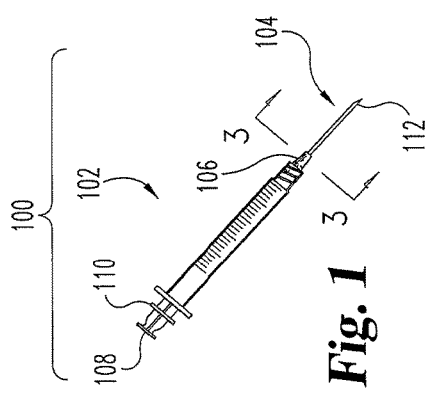
FIG. 2 is a side view of one embodiment of the cell delivery system.

FIG. 2 illustrates another embodiment of a cell delivery system 200. Similar to the embodiments above, system 200 includes a syringe 202 and a hollow needle 204. A connecting member 206 connects syringe 202 and needle 204 and may be an elongated, flexible member such as a tube or catheter. An elongated connecting member 206 would allow needle 204 to be located at a position remote from syringe 202 during the operation of the device 200. Additionally, a flexible connecting member 206 may permit the needle 204 to be advanced in a curvilinear path through a patient's body 500 (e.g. FIG. 5). In some instances, the needle may be advanced through tortuous vasculature inside of a patient's body 500. A first operating member 208 is provided, and may be a plunger or otherwise like member 108.

FIG. 2 also illustrates a second operating member 210 in a particular embodiment. In that embodiment, second operating member 210 is not located on the syringe 202. Having the operating member 210 separate from syringe 202 allows for a simpler attachment and/or separation of the syringe 202 from connecting member 206 and/or needle 204. The arrangement of operating member 210 in this embodiment may also allow for easier connection to an additional device for operation of priming portion 212 of needle 204, such as a mechanical, electrical, thermal, or light energy source. For example, as indicated previously, operating member 210 may be connected to a second syringe, a motor, an actuator, an electrical, thermal, and/or light source.

Figure 3:
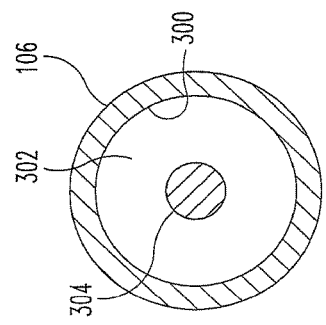
FIG. 3 is a cross-sectional view of a connecting member.

FIG. 3 illustrates an embodiment of connecting member 106. In this embodiment, the connecting member 106 includes a wall 300 that defines a central lumen 302. A tip control member 304 may be positioned inside the central lumen 302 and connect the second operating member 110 with the priming portion 112 of the needle 104.

Figure 4:
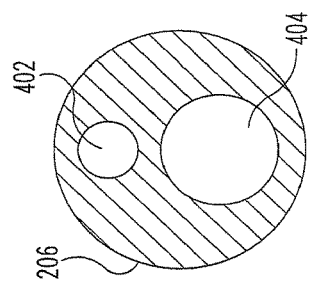
FIG. 4 is a cross-sectional view of a connecting member.

FIG. 4 illustrates another embodiment of connecting member 206. In this embodiment, the connecting member has more than one lumen. For example, the connecting member 206 may include a control lumen 402 and a fluid delivery lumen 404. The control lumen 402 may be used to house one or more members used for communication between the second operating member 210 and the priming portion 212 of the needle 204. The fluid delivery lumen 404 is in fluid communication with the first operating member 208 and is arranged to deliver a material from the syringe 202 through the connecting member 206 to the needle 204. For example, the fluid delivery lumen may deliver a sterilizing agent, a saline solution, or cells through the device 200.

Figure 5:
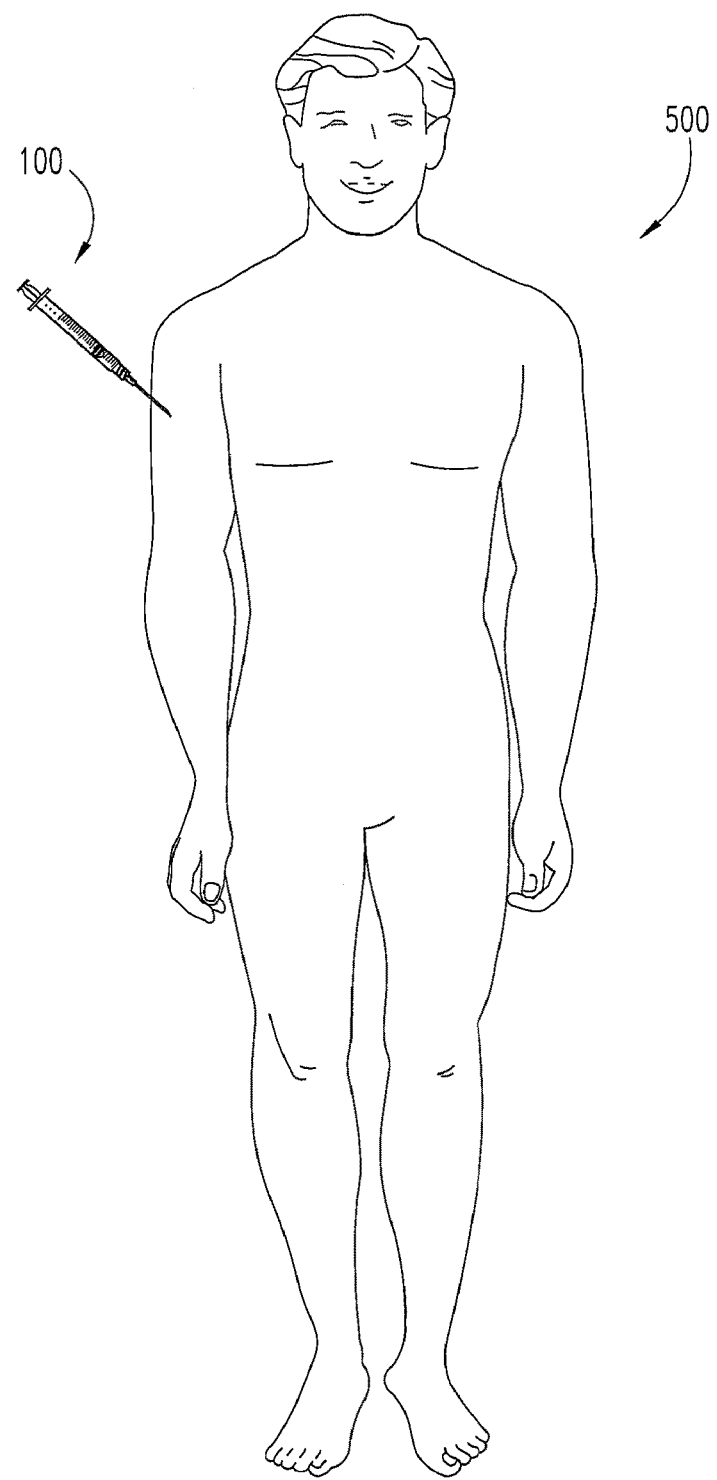
FIG. 5 is a view of one environment of the cell delivery system.

FIG. 5 illustrates one environment in which the system 100 or 200 may be used. In this example, system 100 or 200 is being used to deliver cells to the body 500 of a patient. Needle 104 or 204 is inserted to an internal location where therapy is desired. Cell delivery system 100 or 200, however, may be used in other environments as well. For example, system 100 or 200 may be used to deliver cells to the tissue of an organ transplant and/or the transplant site, prior to the organ being implanted in the patient.

Figure 6:
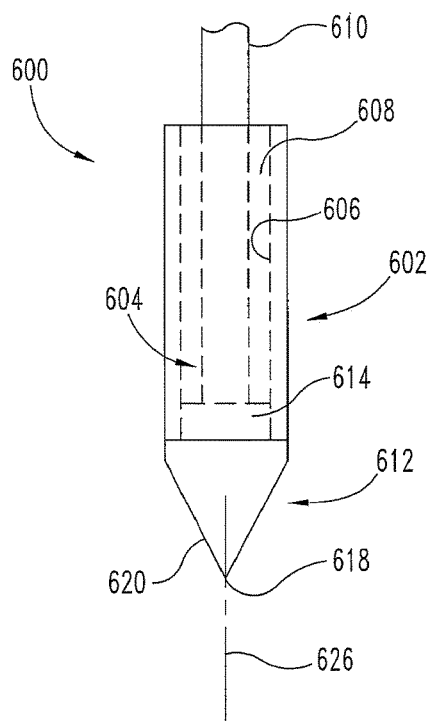
FIG. 6 is a plan view of one embodiment of a needle in a first position.
Figure 7:
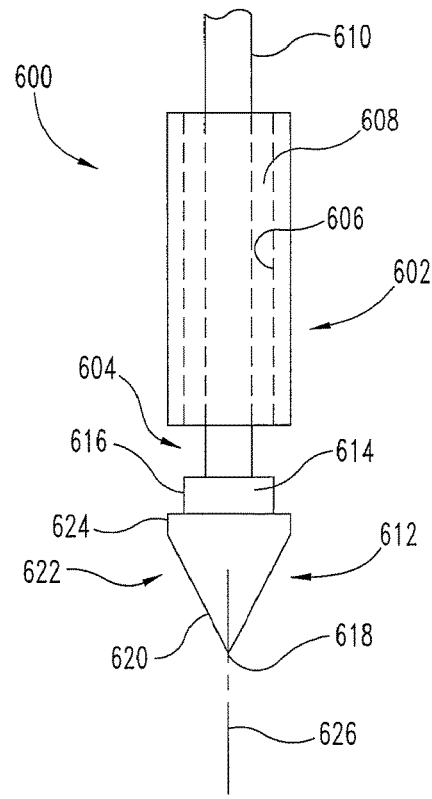
FIG. 7 is a plan view of one embodiment of a needle in a second position.
Figure 8:
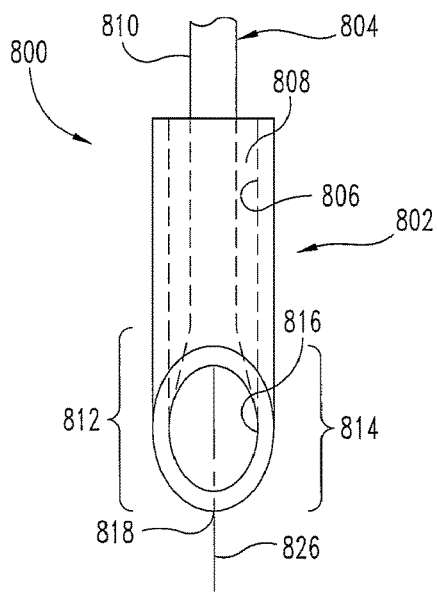
FIG. 8 is a plan view of one embodiment of a needle in a first position.
Figure 10:
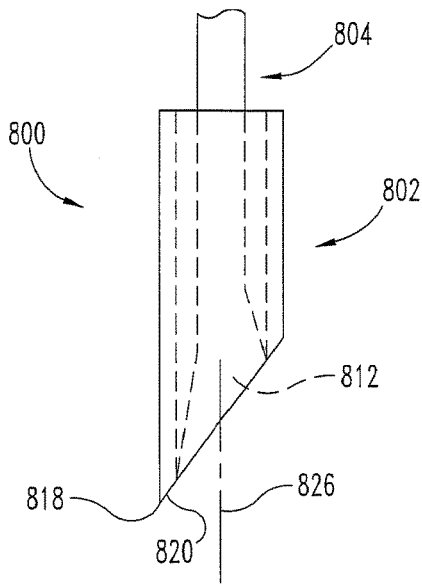
FIG. 10 is a side view of one embodiment of a needle in a first position.
Figure 9:
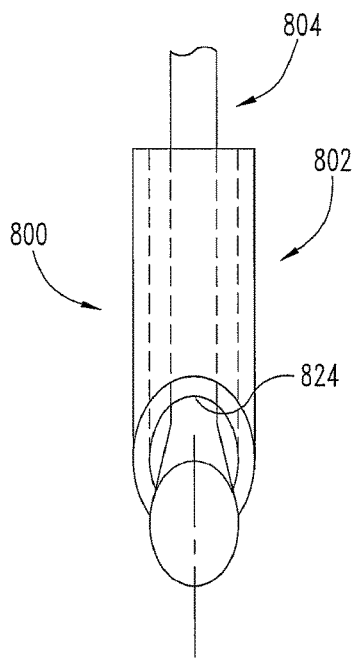
FIG. 9 is a plan view of one embodiment of a needle in a second position.
Figure 11:
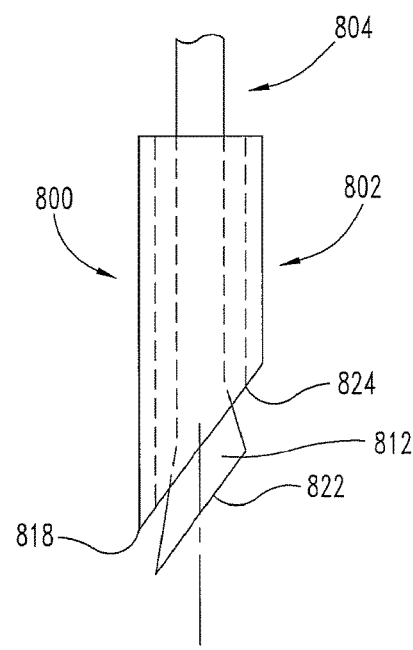
FIG. 11 is a side view of one embodiment of a needle in a second position.
Figure 12:
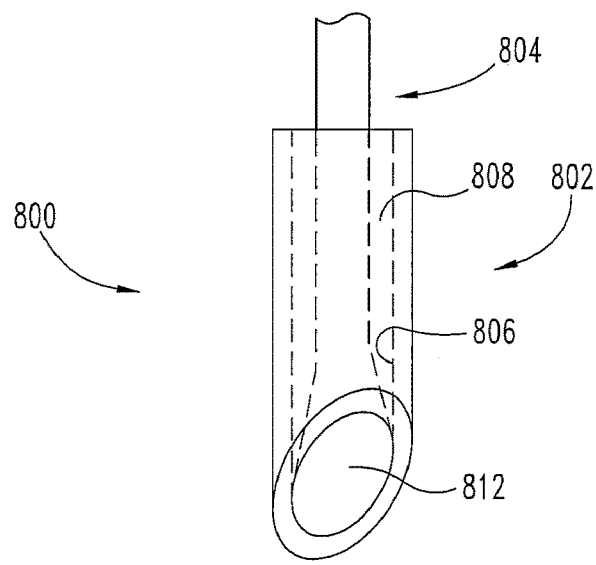
FIG. 12 is a perspective view of one embodiment of a needle in a first position.
Figure 13:
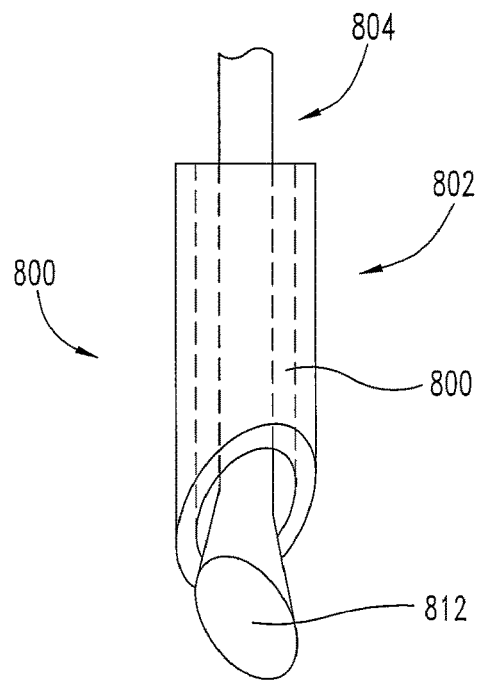
FIG. 13 is a perspective view of one embodiment of a needle in a second position.

FIGS. 6 and 7 illustrate one embodiment of a needle 600 that can be a part of an embodiment of systems such as 100 or 200. In this embodiment needle 600 may be moved or reconfigured from a first configuration (e.g. FIG. 6) to a second configuration (e.g. FIG. 7). Preferably, the needle 600 is in the first configuration during insertion and then is transitioned to the second configuration within the body, before or as it is used to prepare a desired tissue area or body portion and deliver cells. Alternatively, the needle 600 may transition to the second configuration after being used to prime adjacent or surrounding tissue and before or during releasing cells.

The illustrated embodiment of needle 600 includes a sheath portion 602 and a central carrier portion 604. The sheath portion 602 includes at least one interior surface 606 that defines at least one cavity 608 in which the central carrier portion 604 is positioned. Sheath portion 602 may have a closed top, and/or extend outside of the body so that cells or other material in cavity 608 is not open to the body before release of the cells or material is desired. Cavity 608 is used to hold a plurality of cells when needle 600 is in the first configuration, i.e. when cavity 608 is not open to surrounding tissue. When needle 600 is in the second configuration, cavity 608 is open to the adjacent tissue to allow cells to be introduced toward the tissue. Cavity 608 also may communicate with a lumen 302 or 404 in the connecting portion 106 or 206 and first operating member 108 or 208 of the syringe 102 or 202. Cavity 608 may be preloaded with cells after manufacture or loaded with cells immediately prior to the cell delivery procedure. The cells may be flushed from or through cavity 608 during the procedure.

The central carrier portion 604 includes a carrier shaft 610 in this embodiment, which terminates at a nose portion 612. The nose portion 612 has a coupling portion 614 to detachably couple the central carrier portion 604 from the sheath portion 602 of the needle 600. For example, the coupling portion 614 may include at least one coupling surface 616 arranged to abut the interior surface 606 of the sheath portion 602 such that the two are connected in a slip-fit fashion. The coupling portion 614 serves to seal one end of cavity 608. Coupling portion 614 may also align central carrier portion 604 inside the sheath portion 602. As illustrated in FIG. 6, coupling portion 614 aligns the central carrier portion 604 centrally within cavity 608 so that central carrier portion 604 and sheath portion 602 share a longitudinal axis 626. Alignment of the central carrier portion 604 and sheath portion 602 allows the needle assembly to maintain a continuous, smooth transition on its outside surface from the nose portion 612 to the sheath portion 602.

The nose portion 612 may include a tissue penetration portion 618 which may be a sharpened distal end point, surface or tip, and a tissue separating portion 620 adjacent to the tissue penetrating portion 618. The tissue penetration portion 618 in this embodiment is arranged to penetrate the surface of tissue, e.g. skin, muscle, bone, and/or other tissue(s) leading to a desired therapy location, while the tissue separating portion 620 is arranged to separate the tissue to make room for the larger portions of the nose portion 612 and the sheath portion 602. It will be understood that a path to a therapy location may be made by another needle or device (not illustrated), and needle 600 may be inserted with or through such other needle or device or otherwise placed through that path.

The nose portion 612 includes a priming portion 622 that is adjacent to the tissue penetrating portion 618 in this embodiment. Priming portion 622 is arranged to affect the tissue adjacent to the priming portion 622, as by generating a repair or regeneration process at the affected site. The priming portion 622 may include a number of features to facilitate a regeneration response in the tissue adjacent to the priming portion 622. For example, the priming portion 622 may include an abrasive surface used to scratch, score, irritate, or otherwise rub or abrade adjacent tissue; a lip or edge 624 used to pinch tissue between the edge 624 and the sheath 602; one or more edges or raised portions to shallowly tear or cut adjacent tissue; one or more holes and/or ports arranged to deliver a fluid pressure to adjacent tissue; and/or one or more members, such as an electrical and/or thermal conductor, to deliver electrical or thermal energy to adjacent tissue.

The needle 600 and its components may be operated in a variety of ways depending on the configuration of priming portion 622. As one example, priming portion 622 comprises an abrasive surface or raised portions, and priming portion 622 is operated in a rotational motion and/or actuated along its longitudinal axis 626 with respect to adjacent tissue and/or the sheath portion 602, to contact the adjacent tissue. The carrier shaft 610 may be pushed, pulled, and/or turned, as examples, to operate priming portion 622, so as to abrade, pinch, cut or otherwise prime tissue for accepting cells as indicated above. Alternatively or in conjunction, the pressure inside the cavity 608 may be operated so as to transition the needle 600 at least partially between a first configuration (e.g. FIG. 6) to the second configuration (e.g. FIG. 7), or vice-versa. If the priming portion 622 comprises one or more holes and/or ports arranged to deliver fluid pressure, then the system 100 or 200, needle 600, and/or priming portion 622 may be operated to deliver one or more pressure pulses from the holes and/or ports toward the adjacent tissue. If the priming portion 622 comprises one or more members to deliver electrical, thermal, and/or light energy (e.g. laser), the system 100/200, needle 600, and/or priming portion 622 may be operated to energize and then deenergize at least one or more members or transmit light prior to or during the delivery of cells.

FIGS. 8-13 illustrate another embodiment of a needle 800. In this embodiment, needle 800 is operated from a first condition or configuration (e.g. FIGS. 8, 10, and 12), to a second condition or configuration (e.g. FIGS. 9, 11, and 13). Needle 800 may be in the first configuration during insertion and then transitions to the second configuration before or during operation to prime tissue site(s) and/or to deliver cells or cellular material.

Needle 800 includes at least a sheath portion 802 and a central carrier portion 804. Sheath portion 802 has an interior surface 806 that defines a cavity 808. Sheath portion 802 also includes a tapered distal region 814. Region 814 terminates at a tissue penetrating distal tip 818. Central carrier portion 804 has a carrier shaft 810 and an end region 812. End region 812 of the central carrier portion 804 is outwardly tapered in this embodiment to contact interior surface 806 of sheath portion 802 along a substantially flush contact area 816. Contact 816 is near or in distal region 814. Preferably, contact 816 provides for a continuous, smooth transition on the outside surface of the needle 800 from the sheath portion 802 to the central carrier portion 804 in the distal region 814. Preferably, the continuous transition is substantially free of an edge along contact 816. Contact 816 positions central carrier portion 804 centrally inside cavity 808 and seals one end of cavity 808. When needle 800 is being inserted through tissue of a patient in its first configuration, contact 816 prevents trailing edge 824 from causing additional trauma to that tissue.

Sheath portion 802 has a tissue separating portion 820 adjacent to the tissue penetrating distal tip 818. Central carrier portion 804 has a priming portion 822 adjacent to the tissue penetrating distal tip 818. In some embodiments, priming portion 822 is operated in a rotational motion and/or actuated along its longitudinal axis 826 with respect to the adjacent tissue and/or the sheath portion 802. For example, the carrier shaft 810 may be pushed, pulled, and/or turned to operate priming portion 822, as by pressing or rubbing portion 822 against the tissue of interest in particular embodiments. Pressure inside cavity 808 may also be permitted to escape from the contact 816 and prime adjacent tissue (generating a repair or healing response) when the sheath portion 802 and central carrier portion 804 are transitioning and/or have transitioned from the first position to the second position. In the first configuration (FIGS. 8, 10, 12) cells or cellular material are held in cavity 808, while in the second configuration (FIGS. 9, 11, 13) cells or cellular material exit cavity 808 to a desired site, e.g. a site prepared through use of needle 800.

Figure 14:
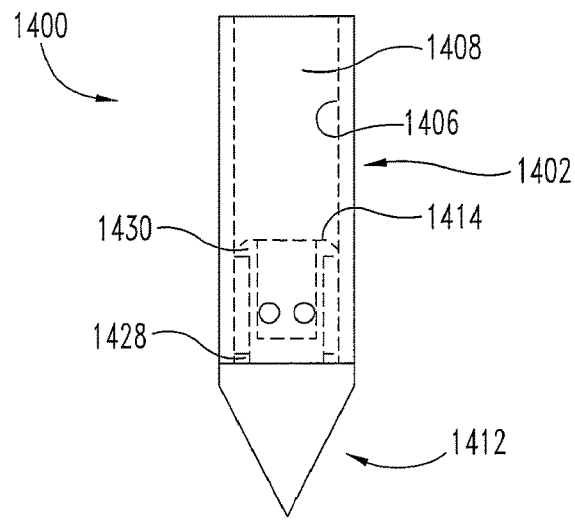
FIG. 14 is a plan view of one embodiment of a needle in a first position.
Figure 15:
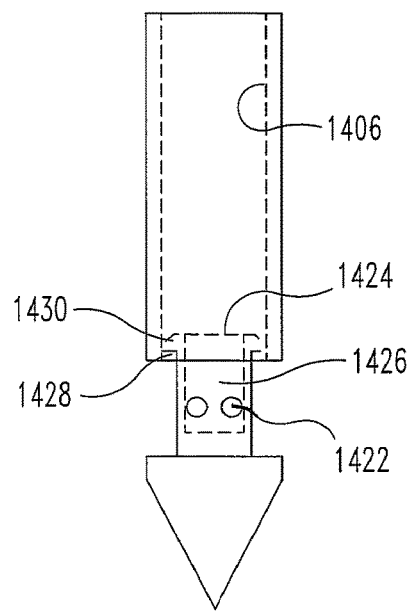
FIG. 15 is a plan view of one embodiment of a needle in a second position.

FIGS. 14 and 15 illustrate an embodiment of a needle 1400 having a body portion 1402 with an interior surface 1406 that defines cavity 1408 and a nose portion 1412. Cavity 1408 is sealed at one end by surface 1414 of nose portion 1412 when needle 1400 is in a first configuration (e.g. FIG. 14) in which nose portion 1412 of needle 1400 is actuated by fluid pressure inside cavity 1408. When cavity 1408 is pressurized, pressure acts on surface 1414 of the nose portion 1412 to actuate the nose portion 1412 from its location in the first configuration (e.g. FIG. 14) to its location in the second configuration (e.g. FIG. 15). When nose portion 1412 is in the second configuration, fluid from cavity 1408 travels into aperture 1424 on surface 1414, through cavity 1426, and exits out of holes or ports 1422.

Interior surface 1408 of needle 1400 has a stop member 1428. Stop member 1428 interacts with catch member 1430 of the nose portion 1412 to prevent the nose portion 1412 from completely separating from body portion 1402. Stop member 1428 and catch member 1430 may be protrusions that abut one another in the second position. Alternatively, stop member 1428 may be a groove and catch member 1430 may be a biased member that enters the stop member 1428, or vice-versa, in the second position.

Figure 16:
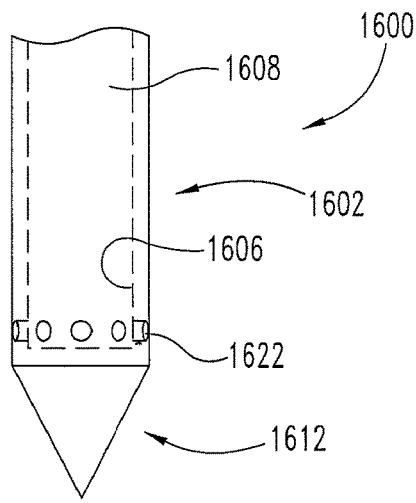
FIG. 16 is a plan view of one embodiment of a needle prior to fluid ejection.
Figure 17:
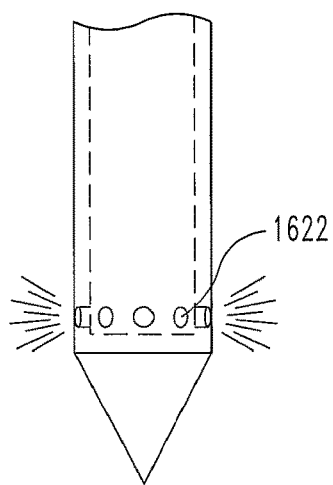
FIG. 17 is a plan view of one embodiment of a needle during fluid ejection.

FIGS. 16 and 17 are an illustration of an embodiment in which a needle 1600 comprises a sheath portion 1602 and a nose portion 1612. Sheath portion 1602 has an interior surface 1606 that defines a cavity 1608. Cavity 1608 is in fluid communication with ports or holes 1622 and a fluid delivery lumen (not illustrated) which is fluidly connected to an operating member (not illustrated). The operating member forces fluid through the fluid delivery lumen into cavity 1608 and through holes 1622 toward the adjacent tissue.

Figure 18:
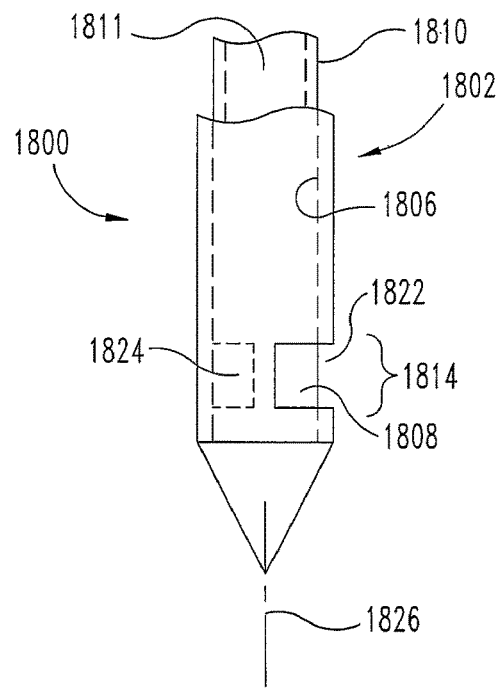
FIG. 18 is a plan view of one embodiment of a needle in a first position.
Figure 19:
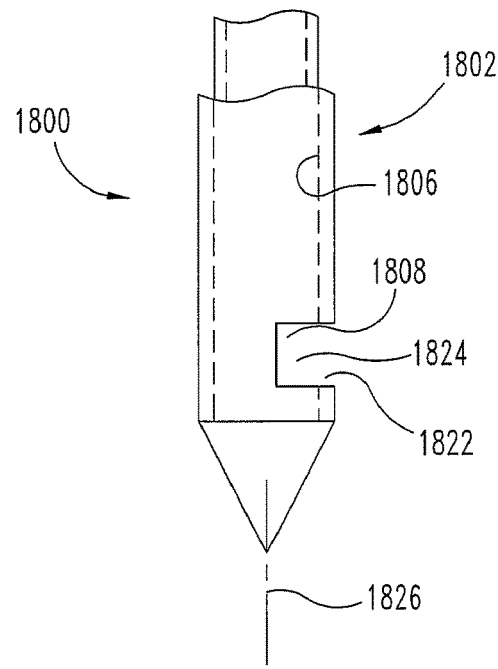
FIG. 19 is a plan view of one embodiment of a needle in a second position.

FIGS. 18 and 19 illustrate an embodiment of a needle 1800 having a sheath portion 1802 and a hollow shaft portion 1810 that rotatingly transition around a longitudinal axis 1826 from a first configuration or relative position (e.g. FIG. 18) to a second configuration or relative position (e.g. FIG. 19). Sheath portion 1802 comprises an interior surface 1806 that defines a first cavity 1808. Hollow shaft portion 1810 has a second cavity 1811. Shaft portion 1810 is located inside the first cavity 1808 and substantially abuts interior surface 1806 of sheath portion 1802 at a discharge region 1814. The close abutment of shaft portion 1810 and interior surface 1806 substantially inhibits the contents of second cavity 1811 from leaking between shaft portion 1810 and interior surface 1806 and out of the port or hole 1822 in sheath portion 1802.

FIG. 18 indicates an example of an insertion configuration. When needle 1800 is in position for insertion into the body, shaft portion 1810 is rotated with respect to sheath portion 1802, aligning hole 1822 in sheath portion 1802 with hole 1824 in shaft portion 1810 to result in the exemplary delivery configuration of FIG. 19. When hole 1822 is at least partially aligned with hole 1824, the second cavity 1811 inside the hollow shaft portion 1810 is in communication with the tissue adjacent to the discharge region 1814.

Figure 20:
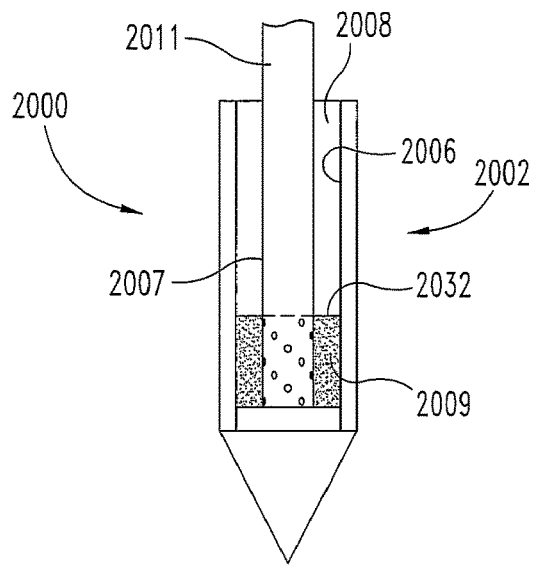
FIG. 20 is a plan view of one embodiment of a needle in a first position.
Figure 21:
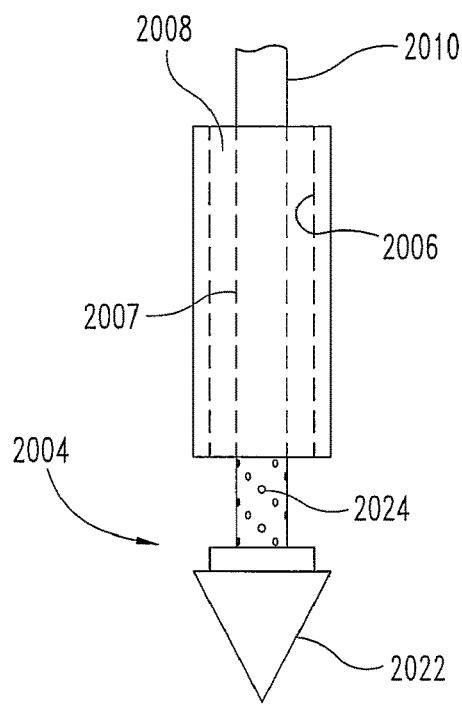
FIG. 21 is a plan view of one embodiment of a needle in a second position.

FIGS. 20 and 21 illustrate an embodiment of a needle 2000 where cells are contained between a sheath portion 2002 and a central carrier portion 2004, and fluid is flushed through the central carrier portion 2004. In this embodiment needle 2000 may be transitioned from a first configuration or relative position illustrated in FIG. 20, to a second position illustrated in FIG. 21. Preferably, needle 2000 is in the first configuration or relative position during insertion, and is transitioned to the second configuration or relative position before or during use to prime adjacent tissue and to deliver cells.

FIGS. 20 and 21 illustrate needle 2000 comprising a sheath portion 2002 and central carrier portion 2004. Sheath portion 2002 has an interior surface 2006. Central carrier portion 2004 is positioned inside sheath portion 2002, and the outer surface 2007 of the central carrier portion 2004 and the interior surface 2006 of the sheath portion 2002 define at least a first cavity 2008 and a second cavity 2009 separated by a seal 2032. Seal 2032 is preferably in a ring or washer shape, surrounds shaft portion 2010, and abuts interior surface 2006 of the sheath portion 2002. Seal 2032 prevents the communication between first cavity 2008 and second cavity 2009. Central carrier portion 2004 has a shaft portion 2010 that defines a shaft cavity 2011. Shaft cavity 2011 is in communication with holes 2024 that open to the second cavity 2009 when the needle is in the first configuration or relative position (e.g. FIG. 20). When the needle is transitioned to the second configuration or relative position (e.g. FIG. 21), holes 2024 are in communication with the tissue surrounding that portion of needle 2000.

Cells (e.g. in an appropriate medium) are preferably preloaded into second cavity 2009 prior to insertion into a patient's body. After needle 2000 has been inserted into the body (e.g. in the first configuration or relative position) and before or during operation of the priming portion 2022, needle 2000 is transitioned to the second configuration or relative position, and cells are released from second cavity 2009 towards the tissue surrounding the needle. Fluid may also be flushed through shaft cavity 2011 inside shaft portion 2010, through holes 2024 to assist in releasing and distributing the cells towards the surrounding tissue.

The needle may also have markers or marker portions to make the device more visible by imaging, such as x-ray or ultrasound, during the procedure. Making the device more visible will enable the operator to more easily determine whether the assembly is in the proper location during insertion, prior to operating the priming member or portion, and/or prior to delivery of the cells from the device. Markers or marker portions may include radiopaque markers such as gold portions to make the device more visible under x-ray. Similarly, the markers or marker portions may include a textured and/or contoured surface to make the device more visible under ultrasound.

The cell delivery assembly may be provided in a kit with at least one or more of the above embodiments and potentially additional equipment. In some instances, such a kit may include the cells or cellular material intended for insertion into a body. For example, the kit may include needles and/or needle assemblies that are preloaded with cells. Alternatively, the cells may be provided in a loadable form, such as a cartridge or an injectable solution, for insertion into the needle prior to delivery of the cells to the target tissue. The cells may be provided in a variety of forms. For example, the cells may be provided in a solution, gel, foam, or sheet and may be configured for loading into/onto the delivery device and/or for delivery to a particular location in the body.

The kit may also provide one or more needles of different sizes, different cell-delivery configurations, and/or different priming portions. Similarly, the kit may provide a variety of syringes and/or energy or pressure sources for operating the needle, delivering the cells, and/or priming the tissue.

The above embodiments may be constructed with biocompatible materials. For example, the entire needle or a portion may be made of a surgical metal, such as stainless steel. Alternatively, the entire needle or a portion may be constructed of a polymer such as polyethelene, polyeheretherketone, or polyimide. There may also be one or more coatings on at least part of the device to facilitate insertion, such as a hydrophilic coating to decrease the friction between the device and the adjacent tissue and/or vasculature. Alternatively, portions of the device may be constructed with a bioabsorbable material. For example, the nose portion may be constructed of a bioabsorbable material that is left in situ after priming tissue and/or delivering cells, such as polycaprolactone, PLA, PGA, chitosan, or SIS (small intestinal submucosa)

Method of Delivery

Prior to the delivery of cells, the user (e.g. physician or other medical professional) selects the delivery site for the cells. For example, if the patient is suffering from a heart attack, the operator may choose a location at or near an infarct zone. For patients suffering from stress urinary incontinence, the operator may choose a target location in or near the striated muscle sphincter (rhabdosphincter).

After selecting the target tissue, the user selects a delivery path. For tissue locations near the patient's skin, the operator may simply choose a direct, percutaneous approach and use an embodiment similar to that in FIG. 1. For target tissue remote from the patient's skin or at a location inaccessible via direct access, the operator may choose an indirect path for insertion. For example, the operator may choose to deliver the device transluminally (e.g. via the esophagus, urethra, or vascular system).

After selecting the delivery path to approach the target tissue, the user prepares the system for cell delivery. Preparation may include selecting a needle size, selecting a priming device or portion (if not already part of the selected needle), selecting the cell-delivery mechanism, and selection of cells or cell material. The operator may pretreat the cells or cell material as may be necessary and/or load it into or onto the device. Loading the cells onto the delivery device may occur immediately prior to insertion of the needle into a patient's body or after the needle has been inserted and/or advanced to the target location, or after the tissue is primed for the cells. Preparing the system may also include preparing or setting any priming portion or device. For example, the operator may fill a syringe with a fluid solution such as saline and attach the syringe to the needle.

The delivery device is operated by bringing the needle tip into close proximity with the surface of a patient's tissue, contacting the needle tip portion with the surface of the tissue, and advancing the needle tip portion into the tissue such that the tissue penetrating distal tip of the needle penetrates the tissue and the tissue separating portion separates the tissue. Preferably, after the needle tip has penetrated the surface of the tissue, imaging, such as x-ray and/or ultrasound, is used to determine the location of the needle. The imaging could be performed one or more times, or continuously, to track the trajectory of the needle through the patient's body prior to delivery of the cells at the target site.

Prior to or during delivery of the cells, the user may operate the priming portion of the cell-delivery system. The priming portion may be operated once or multiple times at one or more locations inside the patient's tissue. For mechanically-operated priming portions (e.g. an abrader or cutter), the priming portion may be actuated relative to another portion of the device and/or in relation to the surrounding tissue. For an priming portion that uses pressure, one or more pressure pulses may be released from the priming portion of the needle prior to the delivery of cells toward the injury tissue. For electrical, thermal, and or light powered priming devices, the operator may deliver one or more pulses of electrical, thermal, or light energy to the target tissue prior to and/or during the delivery of cells.

Releasing the cells may be done by flushing, passive Brownian motion, and/or movement of a portion of the needle assembly. Preferably, the cells are released from the cell delivery portion after the operation of the priming portion to the adjacent prepared tissue. The cells may be released during the operation of the priming portion if it does not significantly affect the newly released cells. For example, if the cells are not adjacent to the priming portion during its operation, the cells may be released during operation of the priming portion. Similarly, the cells may be released during operation of the priming portion and operation of the priming portion ceased when the cells reach the prepared tissue adjacent to the priming portion. In other embodiments, the priming portion may be operated in different priming phases with at least one phase causing an effect different from another phase (quantitatively or qualitatively), and the cells are released during operation of a less-affecting phase. Cells or cell material that join with prepared tissue tend to assist in regeneration, repair or healing or other therapeutic activity, such as bulking.

After operation of the priming portion and/or releasing cells, the needle is retracted from the target tissue. It will be understood that cells may be released (or continue to be released) during retraction of the needle to assist with healing of punctures or tissue damage that may occur in preparing or creating the delivery path or moving the needle along it. During retraction the needle may be in its initial insertion configuration or in its cell-releasing configuration. As indicated above, in some embodiments the needle is retracted in its initial insertion configuration so as to avoid or minimize effects of retraction along the delivery path. In other embodiments, the needle is retracted in its cell-releasing configuration and releases cells along the retraction path.

As used herein, the term "priming" and its variants indicate creating an environment in which a healing cascade, repair or regeneration response or reaction in tissue is initiated, generated or aided, as by disruption of layer(s) of cells (e.g. through abrasion, application of heat or energy, cutting or the like). Similarly, "primed" or "prepared" tissue indicate a receptive site or location for placement of cells or other therapeutic material, e.g. a site at which a healing reaction is generated for acceptance of cells.

While the disclosure has been illustrated and described in detail in the drawings and foregoing description, the same is to be considered as illustrative and not restrictive in character, it being understood that all changes, equivalents, and modifications that come within the spirit of the following claims are desired to be protected. It will be understood that features described particularly with respect to one embodiment are applicable to or with other features or embodiments. Further, features described or depicted herein with identifying numbers having identical last two digits may be considered similar or identical to each other in structure and/or function. All publications, patents, and patent applications cited in this specification are herein incorporated by reference as if each individual publication, patent, or patent application were specifically and individually indicated to be incorporated by reference and set forth in its entirety herein.

What is claimed is:

1. A cell delivery system, comprising: an elongated needle body comprising a sheath having a longitudinal axis, an inner diameter defining a cavity adapted to hold a plurality of cells and a distal end surface, and a central portion partially within the sheath and along the longitudinal axis, the central portion including an end region, the sheath and central portion being movable with respect to each other along or around the longitudinal axis, the sheath terminating in a distal tip adapted for tissue penetration, said sheath and central portion capable of transition from a first configuration for insertion into tissue, in which the end region is positioned within the distal end surface of the sheath to seal the cavity to provide a continuous smooth transition between an external surface of the central portion and an exterior surface of the sheath such that the external surface of the central portion has a flush contact area with the distal surface of the sheath, to a second configuration in which the end region is configured to extend distally from the sheath to open the cavity for delivery of cells when a portion of said body is adjacent a tissue location where therapy is desired, and wherein from the second configuration the central portion is configured to move into the sheath until the end region is positioned within the distal end surface of the sheath, wherein the sheath and central portion are capable of relative rotational movement around the longitudinal axis during transition from the first configuration to the second configuration.

2. The system of claim 1, further comprising:
a first lumen in fluid communication with said cavity.

3. The system of claim 1, wherein:
one or both of the sheath and the central portion move along said longitudinal axis in transitioning from said first configuration to said second configuration.

4. The system of claim 1, further comprising:
a plurality of cells positioned inside said cavity.

5. The system of claim 1, wherein the sheath and central portion are capable of relative translational movement along the longitudinal axis to transition from the first configuration to the second configuration.

6. The system of claim 1, wherein the sheath and central portion are capable of relative rotational movement around the longitudinal axis to transition from the first configuration to the second configuration.

7. The system of claim 1, wherein in the second configuration delivery of cells can occur through a separation between the end region and the sheath.

8. The system of claim 1, wherein the central portion includes a priming portion, and wherein the central portion is movable with respect to the sheath and with respect to tissue adjacent the priming portion at the same time.

9. The system of claim 1, further comprising:
a priming portion adjacent to said tissue penetrating distal tip;
wherein said priming portion is arranged to generate a healing or regeneration response in tissue adjacent to said priming portion prior to the arrival of cells from said cavity to said tissue.

10. The system of claim 9, wherein:
said priming portion comprises at least one fluid ejection port.

11. The system of claim 1, wherein the central portion includes a carrier shaft inside the sheath.

12. The system of claim 11, further comprising a priming portion at a distal portion of the carrier shaft.

13. A cell delivery system, comprising: an elongated body comprising an outer sheath portion defining a cell-carrying portion to hold a plurality of cells, the outer sheath portion terminating at a tissue-penetrating tip arranged to penetrate tissue as the tissue-penetrating tip is forced into bodily tissue, the body further including a central portion extending through the outer sheath portion, the central portion having a distal end region adapted to move along or around a longitudinal axis of said outer sheath portion, the body further having a priming portion positionable adjacent to said tissue-penetrating tip during a first configuration; said outer sheath portion and central portion capable of transition from the first configuration for insertion into tissue, in which the distal end region is fully positioned within the tissue-penetrating distal tip of the outer sheath to seal the cell-carrying portion such that the distal end region of the central portion has a flush contact area with the tissue-penetrating tip of the outer sheath portion in the insertion configuration to a second configuration in which the distal end region is configured to extend distally from the outer sheath to open the cell-carrying portion for delivery of cells; wherein sail outer sheath portion and said central portion are capable of relative rotational movement around the longitudinal axis during transition from the first configuration to the second configuration.

14. The system of claim 13, further comprising:
a plurality of cells positioned inside said cell-carrying portion.

15. The system of claim 13, wherein:
said priming portion comprises at least one fluid ejection port.

* * * * *